US011191922B2

(12) United States Patent
Lee et al.

(10) Patent No.: US 11,191,922 B2
(45) Date of Patent: Dec. 7, 2021

(54) METHOD AND SYSTEM FOR INDUCING SLEEP

(71) Applicant: KOREA UNIVERSITY RESEARCH AND BUSINESS FOUNDATION, Seoul (KR)

(72) Inventors: Seong-Whan Lee, Seoul (KR); Minji Lee, Seoul (KR); Chae Bin Song, Seoul (KR); No Sang Kwak, Seoul (KR)

(73) Assignee: KOREA UNIVERSITY RESEARCH AND BUSINESS FOUNDATION, Seoul (KR)

(*) Notice: Subject to any disclaimer, the term of this patent is extended or adjusted under 35 U.S.C. 154(b) by 308 days.

(21) Appl. No.: 16/398,640

(22) Filed: Apr. 30, 2019

(65) Prior Publication Data

US 2019/0328996 A1 Oct. 31, 2019

(30) Foreign Application Priority Data

Apr. 30, 2018 (KR) .................. 10-2018-0049648
Sep. 19, 2018 (KR) .................. 10-2018-0112464

(51) Int. Cl.
*A61M 21/02* (2006.01)
*A61B 5/00* (2006.01)
(Continued)

(52) U.S. Cl.
CPC ............ *A61M 21/02* (2013.01); *A61B 5/374* (2021.01); *A61B 5/4812* (2013.01);
(Continued)

(58) Field of Classification Search
CPC .......... A61B 5/7475; A61M 2205/502; A61M 2230/10; A61M 2021/0027;
(Continued)

(56) References Cited

U.S. PATENT DOCUMENTS

2015/0297109 A1* 10/2015 Garten .................. A61B 5/375
600/544

FOREIGN PATENT DOCUMENTS

JP U2607357 Y2 7/2001
KR 10-2004-0047754 A 6/2004
(Continued)

OTHER PUBLICATIONS

Korean Office Action dated Aug. 29, 2019, in connection with the Korean Patent Application No. 10-2018-0112464.

*Primary Examiner* — Christine H Matthews
*Assistant Examiner* — Joshua Daryl D Lannu
(74) *Attorney, Agent, or Firm* — Hauptman Ham, LLP

(57) ABSTRACT

The method for inducing sleep by a sleep inducing system includes acquiring brain signals of a user as sleeping time passes; calculating a functional connectivity value between two channels for each frequency based on the acquired brain signals and performing brain network analysis; determining the stage of sleep of the user based on features of the analyzed brain network; determining a target frequency according to the determined stage of sleep and generating a binaural beat with which the brain signals of the user are induced to the target frequency; combining the generated binaural beat with ASMR information; providing the combined auditory stimulus information to the user; and determining whether the current stage of sleep of the user is maintained at an appropriate proportion with respect to total sleep time, determining whether or not to induce the next stage of sleep, and performing feedback according to the result of determination.

20 Claims, 12 Drawing Sheets

(51) Int. Cl.
*A61B 5/048* (2006.01)
*G16H 40/63* (2018.01)
*A61B 5/374* (2021.01)
*A61M 21/00* (2006.01)

(52) U.S. Cl.
CPC .......... *A61B 5/7203* (2013.01); *A61B 5/7475* (2013.01); *G16H 40/63* (2018.01); *A61M 2021/0027* (2013.01); *A61M 2205/50* (2013.01); *A61M 2205/502* (2013.01); *A61M 2205/52* (2013.01); *A61M 2230/10* (2013.01)

(58) Field of Classification Search
CPC .......... A61M 2230/04; A61M 2205/52; A61M 2230/63; A61M 2205/50; A61M 21/02; A61M 2209/088; A61M 2230/005; G16H 20/70; G16H 40/63; G16H 50/30
See application file for complete search history.

(56) References Cited

FOREIGN PATENT DOCUMENTS

| | | |
|---|---|---|
| KR | 10-1044096 B1 | 6/2011 |
| KR | 10-2012-0108488 A | 10/2012 |
| KR | 10-1457477 B1 | 11/2014 |
| KR | 10-2016-0092889 A | 8/2016 |
| KR | 10-1653910 B1 | 9/2016 |
| KR | 10-1687321 B1 | 12/2016 |
| KR | 10-2017-0017603 A | 2/2017 |
| KR | 10-1712878 B1 | 3/2017 |
| KR | 10-1733286 B1 | 5/2017 |
| KR | 10-2017-0074364 A | 6/2017 |
| KR | 10-1746497 B1 | 7/2017 |
| KR | 10-2017-0100651 A | 9/2017 |

* cited by examiner

METHOD AND SYSTEM FOR INDUCING SLEEP

CROSS-REFERENCE TO RELATED APPLICATION

This application claims the benefit under 35 USC 119(a) of Korean Patent Application Nos. 10-2018-0049648 filed on Apr. 30, 2018 and 10-2018-0112464 filed on Sep. 19, 2018 in the Korean Intellectual Property Office, the entire disclosures of which are incorporated herein by reference for all purposes.

TECHNICAL FIELD

The present disclosure relates to a method and system for inducing sleep, and more particularly to a closed loop system and method for improving the quality of sleep by monitoring brain waves of a user before or during sleep, determining personal characteristics from the brain waves according to the stage of sleep, and providing a personalized auditory stimulus.

BACKGROUND

Sleep is an important activity that helps maintain biorhythms and recover the body. Particularly, melatonin is produced in the brain during sleep and serves to prevent cancer, reduce pressure and stress levels, and strengthen immunity by regulating sleep rhythms as well as perform antioxidative and antiaging activities. As such, high-quality sleep is essential to a healthy life. In this sense, lack of sleep or low-quality sleep may break biorhythms and lower immunity. Examples of sleep disorders include insomnia, hypersomnia, somnambulism, sleep paralysis, and the like. According to the result of a survey on daily average sleep time in each country released by the Organization for Economic Cooperation and Development (OECD) in 2014, South Korea ranked the lowest. Further, according to a report released by the National Health Insurance Service in 2013, the number of patients with sleep disorders has been increasing rapidly. Accordingly, there is a need for a method of accurately determining the stage of sleep and managing the quality of sleep.

Basically, the stages of sleep are classified following the guidelines of the American Academy of Sleep Medicine (AASM). Sleep is roughly classified into Non Rapid Eye Movement (NREM) and Rapid Eye Movement (REM) sleep. The NREM sleep refers to the stage in which there is no rapid eye movement, and is classified into three stages. Stage 1 (NREM1) is the stage between sleep and wakefulness. During Stage 1, brain waves and muscles begin to slow down, and representative brain waves for this stage are theta waves (4 Hz to 7 Hz). Stage 2 (NREM2) is the stage of light sleep and characterized by sleep spindles and K-complexes together with theta waves. The sleep spindles (12 Hz to 14 Hz) and the K-complexes serve to suppress response to outside stimuli and protect sleep. Stage 3 (NREM3) is the stage of deep sleep and also known as slow wave sleep. During this stage, the sleeper is less responsive to the outside environment, and representative brain waves for this stage are delta waves (0.5 Hz to 4 Hz). Stage 3 may be split into Stage 3 and Stage 4 depending on the frequency of delta waves. The REM sleep refers to the stage in which there is rapid eye movement and during which dreams occur. Brain waves in this stage are similar to those of the waking state. However, according to the guidelines of the AASM, the stages of sleep are classified depending on only a change in amplitude of the brain's electrical signals, and, thus, it is impossible to understand the recently discovered stage of dreaming in the NREM sleep.

As a conventional technology for classifying the stages of sleep using bio-signals, Korean Patent No. 10-1044096 (entitled "Apparatus for writing dream story and method for writing the same") relates to an apparatus that determines the stage of sleep based on brain waves (EEG) and eye movements, wakes up a user who meets the conditions of REM sleep by providing a stimulus to the user, and records a story of a dream of the user. However, it cannot classify a dream during NREM sleep, and considering that dreams do not always occur when the user reaches REM sleep, it is not suitable to accurately identify the stages of sleep. Further, in Korean Patent Laid-open Publication No. 10-2017-0100651 (entitled "Device and method for sleep monitoring"), the stages of sleep are classified using bio-signals such as heart rate and respiration signals. However, it is difficult to accurately identify the stages of sleep based on only a change in bio-signals caused by secondary induction from brain signals without signals generated from the brain that is the sleep center controlling consciousness and inducing sleep.

A dream is defined as all of mental activities that occur during sleep and is generally known as occurring in REM sleep. However, a lot of recent studies showed that mental activities also occur in NREM sleep and are not particularly different from those occurring in REM sleep. A conscious experience during REM sleep is commonly defined "dream-like" and it is characterized by emotional load, bizarreness, and vividness. In contrast, a conscious experience during NREM sleep is defined "thought-like". In this case, the mental activity is less emotionally intense and the contents are closer to reality and more fragmented than the dream during REM sleep. Sleep paralysis is a phenomenon many people have experienced, and sleep paralysis is generally considered as occurring when a dream is linked to physical discomfort during NREM sleep. Therefore, it is also very important to measure a dream in NREM sleep. Further, the quality of sleep can be affected by the frequency and duration of dreams during sleep, and dreams are interactions between the conscious and unconscious mind and has been widely used as a tool to figure out the unconsciousness of individuals. Therefore, in order to accurately identify the stages of sleep, a new system capable of determining the stage of sleep based on the level of consciousness of a user instead of the brain's electrical signals is needed.

Examples of conventional technology for inducing deep sleep by measuring and analyzing brain signals generated during sleep include Korean Patent No. 10-1687321 (entitled "Apparatus for inducing sleep and sleep management system comprising the same"), Korean Patent No. 10-1712878 (entitled "Induction system for a sound sleep by EEG monitoring"), and Korean Patent No. 10-1733286 (entitled "Neck pillow for sleep induction and relaxation and method for outputting brainwave inducing signals"). Examples of conventional technology for managing sleep by measuring and analyzing other bio-signals or physical condition include Korean Patent No. 10-1746497 (entitled "Apparatus for inducing sleep and method for inducing sleep using the same"), Korean Patent Laid-open Publication No. 10-2016-0092889 (entitled "Apparatus and method for assisting sound sleep"), and Korean Patent Laid-open Publication No. 10-2017-0074364 (entitled "Apparatus and method for providing sleeping guide"). The above-described patents suggest a system or method for inducing or managing sleep.

However, Korean Patent No. 10-1687321 relates to an apparatus capable of measuring a sleep state based on a brain wave and of adjusting a sleep state of a user by using sound or light. In this case, the apparatus analyzes a sleep state of a user by measuring a brain wave and applies a stimulus to induce a preset frequency for the sleep state. However, a frequency appearing prominently in each stage of sleep varies depending on various characteristics of individuals, which is not considered in this case. Korean Patent No. 10-1712878 relates to a system that uses a technology of measuring and analyzing brain waves and induces a user to sleep using lighting and sound effects suitable for a measured brain wave. The system adjusts lighting and sound of an integrated desk lamp according to a brain wave signal measured using an application in a smartphone. The integrated desk lamp is composed of a three-color LED light source and a speaker. However, the lighting and sound effects do not reflect differences in frequency depending on the stages of sleep in individuals. Korean Patent No. 10-1733286 relates to a neck pillow for inducing sleep and relaxation and a method for outputting brain wave inducing signals using the same. The neck pillow is equipped with speakers on its left and right sides corresponding to positions of a user's head. If the user's head is detected as tilted, the level of sound output from the speaker on one side to which the user's head is tilted or on the other side is adjusted. However, this method induces sleep by providing an acoustic stimulus based on only head-tilt information without identifying the stages of sleep and thus has low reliability. Korean Patent No. 10-1746497 relates to an apparatus and method for inducing sleep by controlling a sleep environment in real time according to a sleep state of a user. The apparatus analyzes a sleep state of a user who wears a bracelet including a pulse sensor, a humidity sensor, a temperature sensor, and a motion sensor therein. The apparatus includes a sound providing unit and a lighting unit to provide a sleep environment suitable for the analyzed sleep state. However, if a sleep state is analyzed using only other bio-signals without measuring brain waves, a mixture of signals from a user and another person sleeping next to the user can be measured. Korean Patent Laid-open Publication No. 10-2016-0092889 relates to a method and apparatus for adaptively adjusting a wake-up time based on sleep state information of a user who is sleeping. The apparatus measures heart rate information, respiration information, movement information, snoring pattern information, eyeball movement information, and body temperature information. However, the apparatus analyzes a sleep state using only other bio-signals without measuring brain waves and induces sound sleep, which results in a low accuracy in analysis. Korean Patent Laid-open Publication No. 10-2017-0074364 relates to an apparatus and method for providing a personalized sleep guide message by comparing a personal sleep pattern with general sleep pattern information. The apparatus senses the movement and sound of a user and the intensity of illumination, temperature and noise in a sleeping place, adjusts a sleep environment, and outputs a sleep guide message. The quality of sleep cannot be sufficiently improved just by outputting a sleep guide message or adjusting other environmental conditions.

The above-described patents have limitations because they suggest stimuli such as sound effects without considering a personal frequency for each stage of sleep, and have a low accuracy in measurement of sleep state because they measure a sleep state based on only state information such as movement information and snoring information of a user during sleep without measuring brain waves.

Accordingly, a representative frequency for each stage of sleep depending on personal characteristics needs to be considered to efficiently improve the quality of sleep. Examples of indices that vary depending on the stages of sleep of each individual include amplitude, power spectrum, sleep spindle density, sleep spindle duration, and the like. These indices also need to be considered to provide a personalized auditory stimulus for each stage of sleep. The movement information or other environmental information during sleep may include information about a target subject and bio or environmental information of another person sleeping in the same place, which may cause various problems.

SUMMARY

In view of the foregoing, the present disclosure provides a method and system that can measure signals from a user using electroencephalogram without other bio-signals such as electrocardiogram or electromyogram, accurately determine the stages of sleep including the stage of dreaming in NREM sleep based on the measured signals using brain connectivity that is changed during transition between conscious and unconscious states, and induce mental stability of the user considering a change in frequency of bio-signals according to the stage of sleep of the user and a change in frequency of bio-signals caused by an auditory stimulus to improve the quality of sleep.

According to a first aspect of the present disclosure, a method for inducing sleep by a sleep inducing system includes: acquiring brain signals of a user as sleeping time passes; calculating a functional connectivity value between two channels for each frequency based on the acquired brain signals and performing brain network analysis; determining the stage of sleep of the user based on features of the analyzed brain network; determining a target frequency according to the determined stage of sleep and generating a binaural beat with which the brain signals of the user are induced to the target frequency; combining the generated binaural beat with autonomous sensory meridian response (ASMR) information; providing the combined auditory stimulus information to the user; and determining whether the current stage of sleep of the user is maintained at an appropriate proportion with respect to total sleep time, determining whether or not to induce the next stage of sleep, and performing feedback according to the result of determination.

According to a second aspect of the present disclosure, a sleep inducing system includes: a memory in which a program configured to perform a method for inducing sleep is stored; and a processor that executes the program, and upon execution of the program, the processor acquires brain signals of a user as sleeping time passes, calculates a functional connectivity value between two channels for each frequency based on the acquired brain signals and performs brain network analysis, determines the stage of sleep of the user based on features of the analyzed brain network, determines a target frequency according to the determined stage of sleep and generates a binaural beat with which the brain signals of the user are induced to the target frequency, combines the generated binaural beat with autonomous sensory meridian response (ASMR) information, provides the combined auditory stimulus information to the user, and determines whether the current stage of sleep of the user is maintained at an appropriate proportion with respect to total sleep time, determines whether or not to induce the next stage of sleep, and performs feedback according to the result of determination.

According to the present disclosure, the stages of sleep can be evaluated according to various characteristic changes of brain connectivity based on a brain network that is changed during sleep of a user, and an auditory stimulus with different frequencies for respective stages of sleep can be provided based on a closed loop system.

Further, according to the present disclosure, the stages of sleep including the stage of dreaming in NREM sleep can be identified accurately and evaluated based on the level of consciousness. Therefore, the reliability of a sleep inducing system is expected to increase.

Furthermore, according to the present disclosure, the stage of sleep of the user can be analyzed in real time and a frequency suitable for the stage of sleep can be provided. Moreover, metal stability can be induced using ASMR auditory stimuli, and, thus, the user can use the system in a more mentally stable state than in the case where auditory stimuli composed of simple beep sounds are provided. Therefore, the method according to the present disclosure can improve the quality of sleep more effectively than the conventional methods.

BRIEF DESCRIPTION OF THE DRAWINGS

In the detailed description that follows, embodiments are described as illustrations only since various changes and modifications will become apparent to those skilled in the art from the following detailed description. The use of the same reference numbers in different figures indicates similar or identical items.

DETAILED DESCRIPTION

Figure 1:
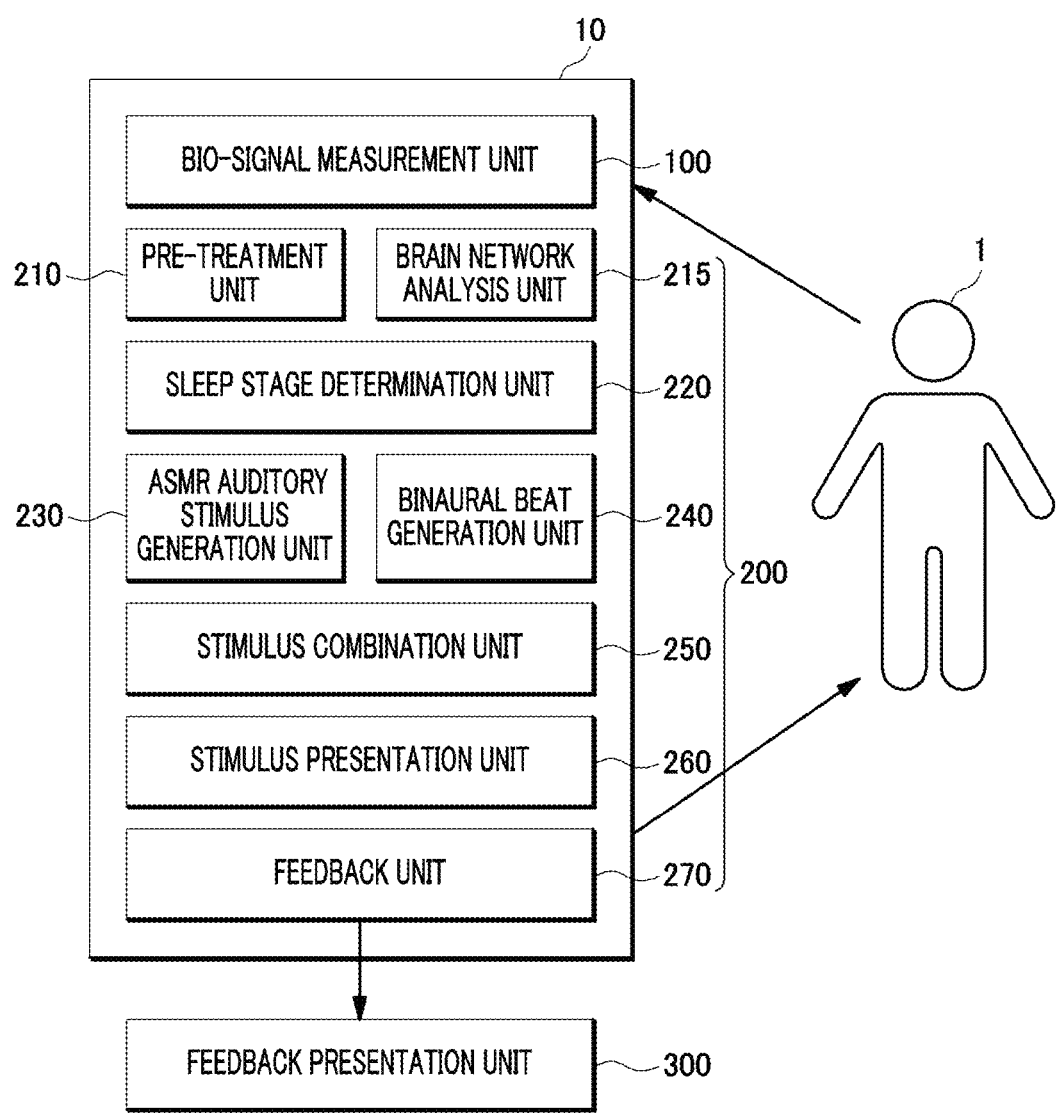
FIG. 1 is a configuration diagram showing a sleep inducing system in accordance with various embodiments described herein.

Hereinafter, embodiments of the present disclosure will be described in detail with reference to the accompanying drawings so that the present disclosure may be readily implemented by a person with ordinary skill in the art. However, it is to be noted that the present disclosure is not limited to the embodiments but can be embodied in various other ways. In drawings, parts irrelevant to the description are omitted for the simplicity of explanation, and like reference numerals denote like parts through the whole document.

Through the whole document, the term "connected to" or "coupled to" that is used to designate a connection or coupling of one element to another element includes both a case that an element is "directly connected or coupled to" another element and a case that an element is "electronically connected or coupled to" another element via still another element. Further, it is to be understood that the term "comprises or includes" and/or "comprising or including" used in the document means that one or more other components, steps, operation and/or existence or addition of elements are not excluded in addition to the described components, steps, operation and/or elements unless context dictates otherwise.

Throughout this document, the term "unit" includes a unit implemented by hardware and/or a unit implemented by software. As examples only, one unit may be implemented by two or more pieces of hardware or two or more units may be implemented by one piece of hardware. Further, the "unit" is not limited to the software or the hardware and may be stored in an addressable storage medium or may be configured to implement one or more processors. Accordingly, the "unit" may include, for example, software, object-oriented software, classes, tasks, processes, functions, attributes, procedures, sub-routines, segments of program codes, drivers, firmware, micro codes, circuits, data, database, data structures, tables, arrays, variables and the like. The components and functions of the "unit" can be combined with each other or can be divided up into additional components and "units". Further, the components and the "units" may be configured to implement one or more CPUs in a device or a secure multimedia card.

A "sleep inducing apparatus" described herein may be implemented with computers or portable devices which can access a server or another device through a network. Herein, the computers may include, for example, a notebook, a desktop, and a laptop equipped with a WEB browser. For example, the portable devices are wireless communication devices that ensure portability and mobility and may include all kinds of handheld-based wireless communication devices such as IMT (International Mobile Telecommunication)-2000, CDMA (Code Division Multiple Access)-2000, W-CDMA (W-Code Division Multiple Access), Wibro (Wireless Broadband Internet), LTE (Long Term Evolution)- based devices, smartphones, tablet PCs, and the like. Further, the "network" may be implemented as wired networks such as a Local Area Network (LAN), a Wide Area Network (WAN) or a Value Added Network (VAN) or all kinds of wireless networks such as a mobile radio communication network or a satellite communication network.

Hereinafter, an embodiment of the present disclosure will be described in detail.

FIG. 1 is a configuration diagram showing a sleep inducing system in accordance with various embodiments described herein.

Referring to FIG. 1, a system 10 according to an embodiment of the present disclosure includes a bio-signal measurement unit 100, a sleep inducing apparatus 200, and a feedback presentation unit 300.

The bio-signal measurement unit 100 measures electroencephalography (EEG) signals through multiple electrodes in contact with or adjacent to a user's scalp to measure an electrical signal that is changed depending on the user's stage of sleep. For example, the bio-signal measurement unit 100 may measure brain signals from the stage of wake-up before sleep.

The bio-signal measurement unit 100 may measure, in real time, a user 1's brain signals that are changed depending on the user 1's stages of sleep and transmit the brain signals to the sleep inducing apparatus 200. Details of the bio-signal measurement unit 100 will be described later with reference to FIG. 2A.

The sleep inducing apparatus 200 is connected wiredly or wirelessly to the bio-signal measurement unit 100 to acquire the user's brain signals as sleeping time passes, performs pre-treatment to the acquired brain signals to be suitable for brain network analysis, calculates a functional connectivity value between two channels for each frequency based on the pre-treated brain signals, and performs brain network analysis. Then, the sleep inducing apparatus 200 determines the stage of sleep of the user based on features of the analyzed brain network and provides the determined stage of sleep of the user through a user interface.

Further, the sleep inducing apparatus 200 determines a target frequency according to the determined stage of sleep and generates a binaural beat with which the brain signals of the user 1 are induced to the target frequency. Then, the sleep inducing apparatus 200 combines the generated binaural beat with autonomous sensory meridian response (ASMR) information, provides the combined auditory stimulus information to the user 1. Then, the sleep inducing apparatus 200 determines whether the current stage of sleep of the user 1 is maintained at an appropriate proportion with respect to total sleep time, determines whether or not to induce the next stage of sleep, and performs feedback according to the result of determination. Therefore, according to the present disclosure, an auditory stimulus with different frequencies for respective stages of sleep can be provided based on a closed loop system. Moreover, metal stability can be induced using ASMR information, and, thus, the user can be in a more mentally stable state than in the case where auditory stimuli composed of simple beep sounds are provided, and the quality of sleep can be improved more effectively by the method according to the present disclosure than by the conventional methods.

The feedback presentation unit 300 visually presents the determined user's stage of sleep to the user through the user interface.

Meanwhile, according to integrated Information theory, under consciousness, information integration is done in the cerebrum, whereas under unconsciousness, electroactive signals are generated but information integration is broken down. When consciousness transitions to unconsciousness, information integration capability of the nervous system is remarkably decreased, and loss of consciousness occurs when spatial-temporal self-organization of brain waves is broken down. Particularly, when consciousness is lost, the amount of information flowing from the frontal lobe in charge of recognition to the occipital lobe in charge of sense is sharply decreased. Such a change in the brain between consciousness and unconsciousness cannot be explained only with simple indices such as potential and frequency amplitude of brain waves.

Accordingly, the present disclosure suggests a method of quantifying interactions among brain nerves important for consciousness and unconsciousness into brain connectivity indices to overcome the problems of the above-described technologies rather than simply analyzing electrical signals from brain. Particularly, the stages of sleep can be determined more accurately based on the level of consciousness by understanding interactions between different regions through brain network analysis and thus understating the stage of dreaming in NREM sleep, which has not been measured. This technology for accurately determining the stages of sleep will provide important factors in measuring the quality of sleep of the user and understanding sleep disorders.

Figure 2A:
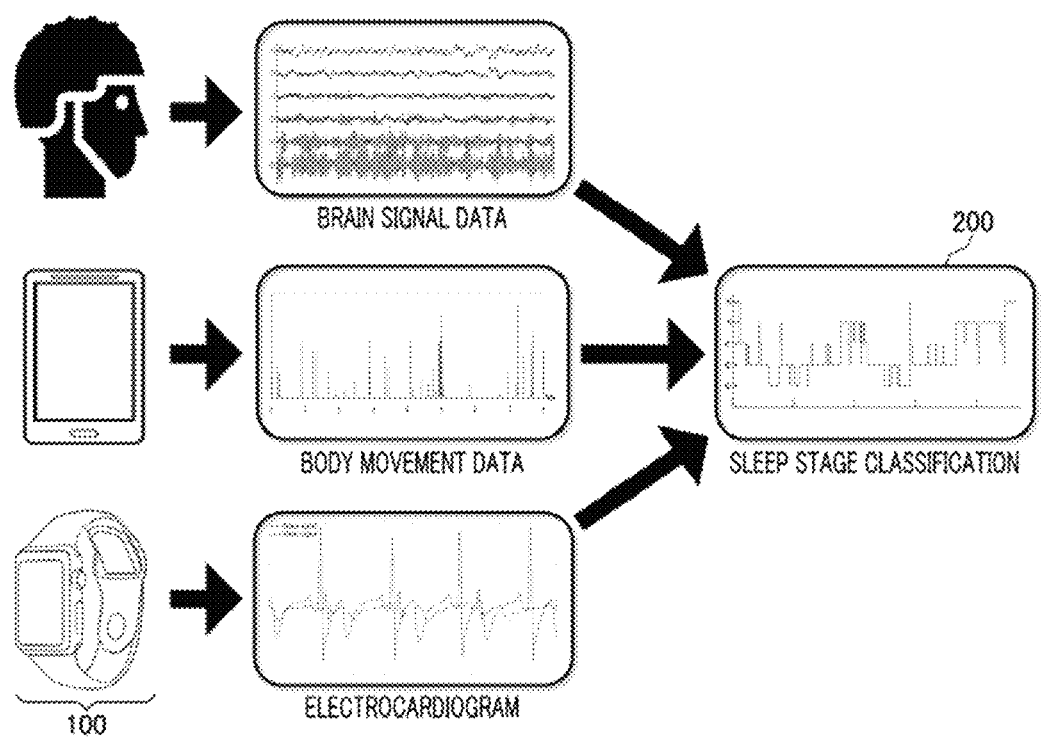
FIG. 2A is an example depiction showing a process for measuring bio-signals during sleep with various devices in accordance with various embodiments described herein.

FIG. 2A is an example depiction showing a process for measuring bio-signals during sleep with various devices in accordance with various embodiments described herein.

Referring to FIG. 2A, the bio-signal measurement unit 100 may include at least one of a smart band, a smartphone, a multi-channel cap for brain signal measurement, and a headband-type brain signal measurement device. Herein, the bio-signals may include one or more of brain signal, pulse, heart rate, and movement of the body. Particularly, brain signals can be measured using any device capable of measuring brain signals from the frontal lobe which refers to a front part of the head including the forehead.

A pre-treatment unit 210 may receive, from the bio-signal measurement unit 100, the user's bio-signals as sleeping time passes. Further, the pre-treatment unit 210 may remove noise from the bio-signals and perform filtering to the noise-removed bio-signals in a specific frequency band related to sleep or consciousness.

For example, the bio-signals may be analyzed in a time window of 30 seconds. If the bio-signals are measured using a smart band, PQRST waveforms which are electrocardiographic waveforms can be analyzed using singular value decomposition, Hilbert-Huang transform, or the like.

Hereinafter, the configuration of the sleep inducing apparatus 200 based on the level of consciousness using brain connectivity in accordance with various embodiments described herein will be described in detail with reference to FIG. 2B through FIG. 10.

Figure 2B:
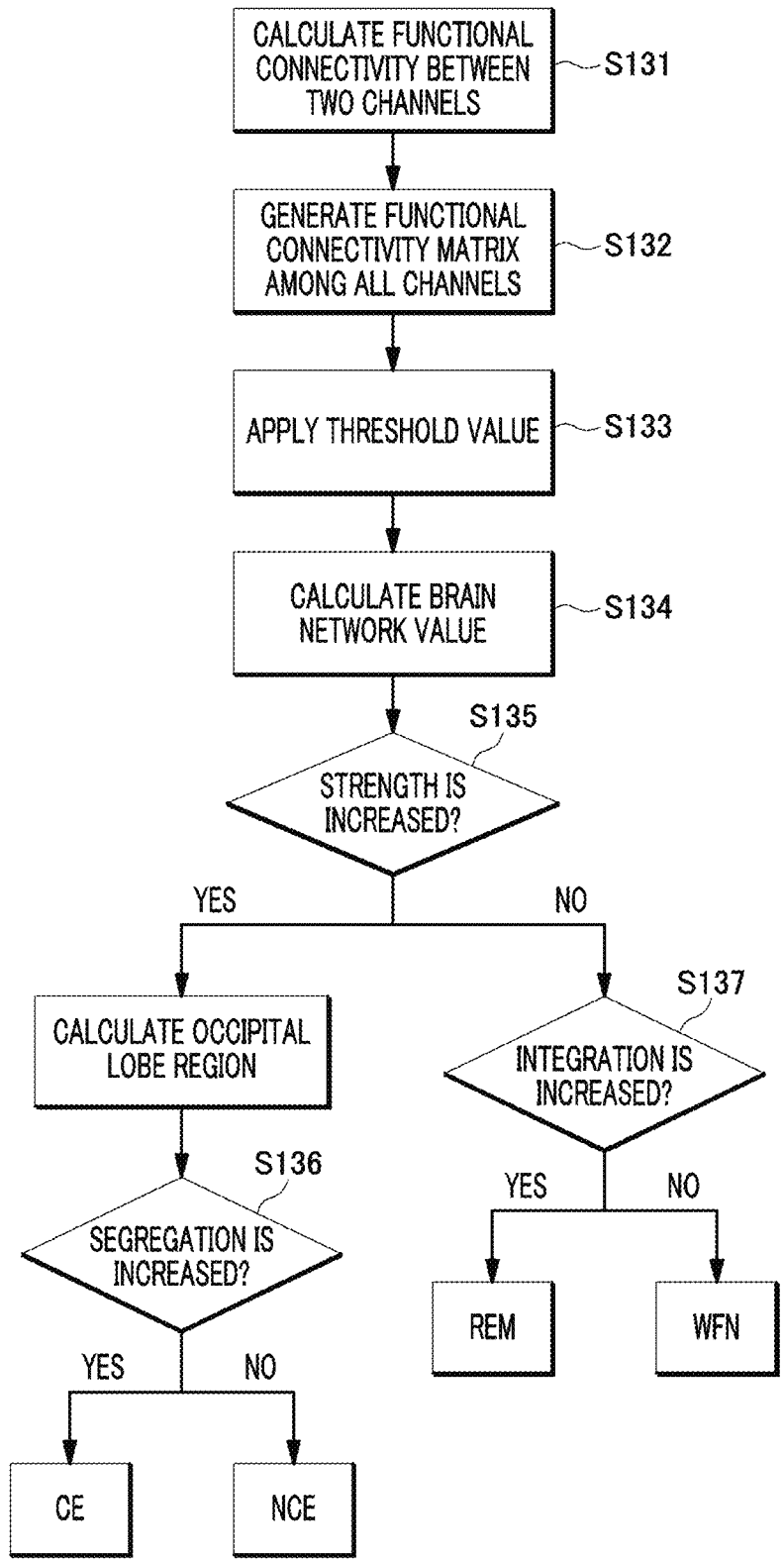
FIG. 2B is a flowchart provided to explain a method for performing brain network analysis by a sleep inducing apparatus in accordance with various embodiments described herein.

FIG. 2B is a flowchart provided to explain a method for performing brain network analysis by a sleep inducing apparatus in accordance with various embodiments described herein.

Referring to FIG. 1 again, the sleep inducing apparatus 200 may include a memory configured to perform a method for inducing sleep using brain signals of the user 1 and a processor configured to execute a program (or an application) stored in the memory. Herein, the processor may perform various functions upon execution of the program stored in the memory, and may include the pre-treatment unit 210, a brain network analysis unit 215, a sleep stage determination unit 220, an ASMR auditory stimulus generation unit 230, a binaural beat generation unit 240, a stimulus combination unit 250, and a feedback unit 270 as submodules for the respective functions.

The pre-treatment unit 210 receives, from the bio-signal measurement unit 100, the user's brain signals as sleeping time passes. The brain signals may be EEG signals measured through electrodes in contact with or adjacent to the user's scalp. Further, the pre-treatment unit 210 may remove noise caused by head and eyeball movements or eye blink from the measured brain signals and perform filtering to the noise-removed brain signals in a specific frequency band related to sleep or consciousness.

Referring to FIG. 2B, the brain network analysis unit 215 may calculate a functional connectivity value between two channels for each frequency based on amplitude and phase values of the respective pre-treated brain signals (S131), apply a threshold value to determine whether or not the calculated functional connectivity value has significant connectivity (S133), and calculate a brain network value based on the graph theory (S134). Further, the brain network analysis unit 215 may measure a feature of a brain network for each of the frontal lobe and the occipital lobe based on the calculated brain network value (S135).

Herein, in process S131, the functional connectivity value is a criterion to determine the degree of synchronization of phases between brain signals of the two channels and may include a phase locking value, a phase lag index, a weighted phase lag index, an imaginary coherence, and a synchronization likelihood. To be specific, in process S132, functional connectivity values among all the channels for each frequency can be calculated into a matrix based on the calculated value. Further, in process S133, the connectivity equal to or less than a specific threshold value is converted into 0 to find out only the significant functional connectivity. Then, in process S134, a brain network value based on the graph theory is calculated from the functional connectivity matrix that represents only the significant connectivity. The brain network value refers to a quantified value of the connectivity in the brain.

Further, the threshold value may be set to a value with the greatest difference between a global efficiency and a local efficiency calculated from multiple (desirably, 1000 or more) random matrixes.

For example, brain network values are graph theory values known in the graph theory field. For example, the global efficiency is an integration criterion of brain connectivity and represents the efficiency of information integration flow in the entire cerebrum, and the local efficiency is a segregation criterion of brain connectivity and represents the network efficiency of information integration flow in a specific region of the cerebrum. Further, the brain network values are not limited thereto and may include at least one of graph theory values such as characteristic path length, clustering coefficient, node degree, betweenness centrality, and node centrality that represent various features of brain connectivity.

For example, the brain network value may be a criterion to determine the degree of integration of brain network and may be quantified into one or more of global efficiency and characteristic path length.

The following Equation 1 represents the global efficiency.

$$E_{glob} = \frac{1}{N(N-1)} \sum_{i \neq j} \frac{1}{d_{ij}} \quad \langle \text{Equation 1} \rangle$$

Herein, N represents the number of columns in a functional connectivity matrix, and $d_{ij}$ represents the length of the shortest path between nodes i and j.

The following Equation 2 represents the characteristic path length.

$$L = \frac{1}{N} \sum_{i \in N} L_i = \frac{1}{N} \sum_{i \in N} \frac{\sum_{j \in N, j \neq i} d_{ij}}{n-1} \quad \langle \text{Equation 2} \rangle$$

Herein, N represents the number of all nodes, $d_{ij}$ represents the length of the shortest path between nodes i and j, and $L_i$ represents the average distance value between the node i and all the other nodes.

For example, the brain network value may be a criterion to determine the degree of segregation of brain network and may be quantified into one or more of local efficiency, clustering coefficient, transitivity, and modularity.

The following Equation 3 represents the local efficiency and includes Equation 1.

$$E_{loc} = \frac{1}{N} \sum_i E_{globe}(A_i) \quad \langle \text{Equation 3} \rangle$$

Herein, N represents the number of columns in a functional connectivity matrix, and $A_i$ represents a subgraph between a node i and its neighbors.

The following Equation 4 represents the clustering coefficient.

$$C = \frac{1}{n} \sum_{i \in N} C_i = \frac{1}{N} \sum_{i \in N} \frac{2t_i}{k_i(k_i-1)} \quad \langle \text{Equation 4} \rangle$$

Herein, n represents the number of corresponding nodes, N represents the number of all nodes, $t_i$ represents the number of triangles formed by a node i, and $C_i$ represents a clustering coefficient of the node i.

The following Equation 5 represents the transitivity.

$$T = \frac{\sum_{i \in N} 2t_i}{\sum_{i \in N} k_i(k_i-1)} \quad \langle \text{Equation 5} \rangle$$

Herein, N represents the number of all nodes, $t_i$ represents the number of triangles formed by a node i, and $k_i$ represents the number of links linked to the node i.

For example, the brain network value may be a criterion to determine the degree of functional connectivity between one of multiple nodes in a brain network and the other nodes and may be quantified into one or more of node degree and strength. The nodes may be the electrodes of the bio-signal measurement unit 100.

The strength refers to the average value of brain connectivities for the respective nodes. For example, the node degree is similar to the strength and may be used as an index to firstly identify REM sleep state/WFN state (waking state), and NREM sleep state, instead of the strength value.

As shown in FIG. 2B, the sleep stage determination unit 220 may identify the stages of sleep as WFN (Wakefulness)

state, REM (Rapid Eye Movement) sleep state, and CE (Conscious Experience) state and NCE (No Conscious Experience) state in NREM (Non Rapid Eye Movement) sleep state based on the brain network value. To be specific, the sleep stage determination unit 220 may determine the stages of sleep of the user as sleeping time passes based on the strength which is the average value of brain connectivities for the respective nodes (S135). Herein, the WFN state refers to a waking state, the REM sleep state refers to where most of dreams occur and there is rapid eye movement. In the NREM sleep state, the CE state refers to where we encounter dream-like conscious experiences and the NCE state refers to where we do not encounter any conscious experience.

That is, in process S135, two stages of sleep, i.e., the REM sleep state and WFN state in which there is rapid eye movement in the frontal lobe region and the NREM sleep state in which there is no rapid eye movement in the occipital lobe region may be firstly identified based on the strength value.

Figure 3:
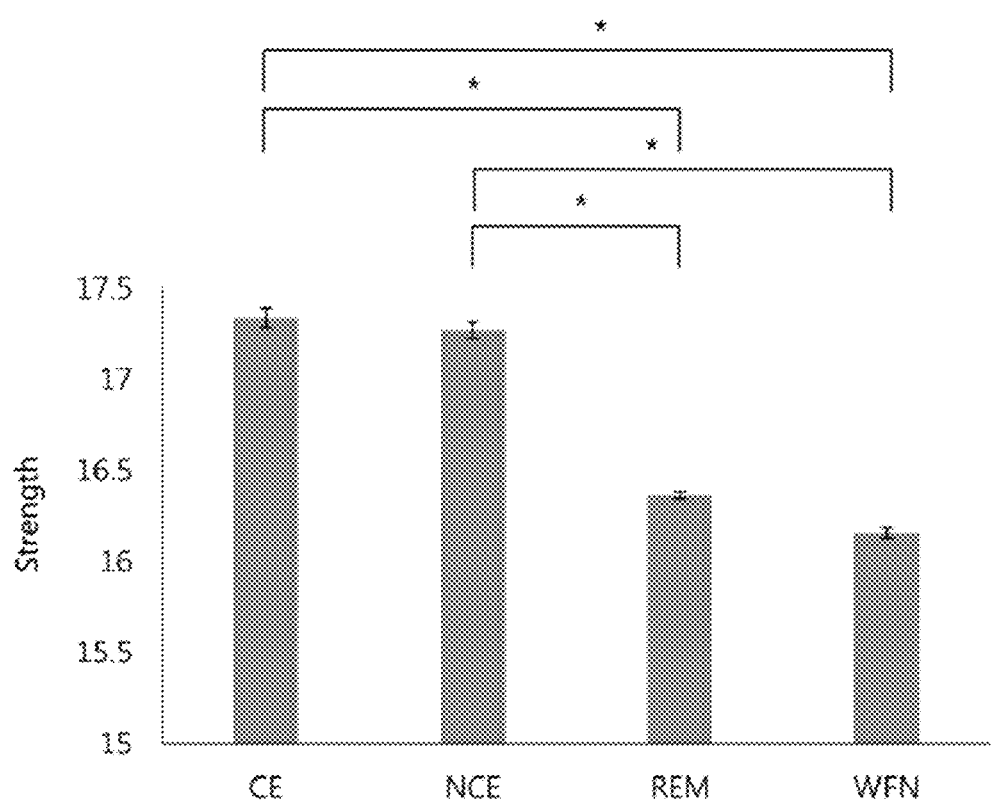
FIG. 3 is a graph showing a change in strength depending on the stage of sleep classified into a WFN state, a REM sleep state, and a CE state and a NCE state of a NREM sleep state in accordance with various embodiments described herein.

FIG. 3 is a graph showing a change in strength depending on the stage of sleep classified into a WFN state, a REM sleep state, and a CE state and a NCE state of a NREM sleep state in accordance with various embodiments described herein.

Figure 4:
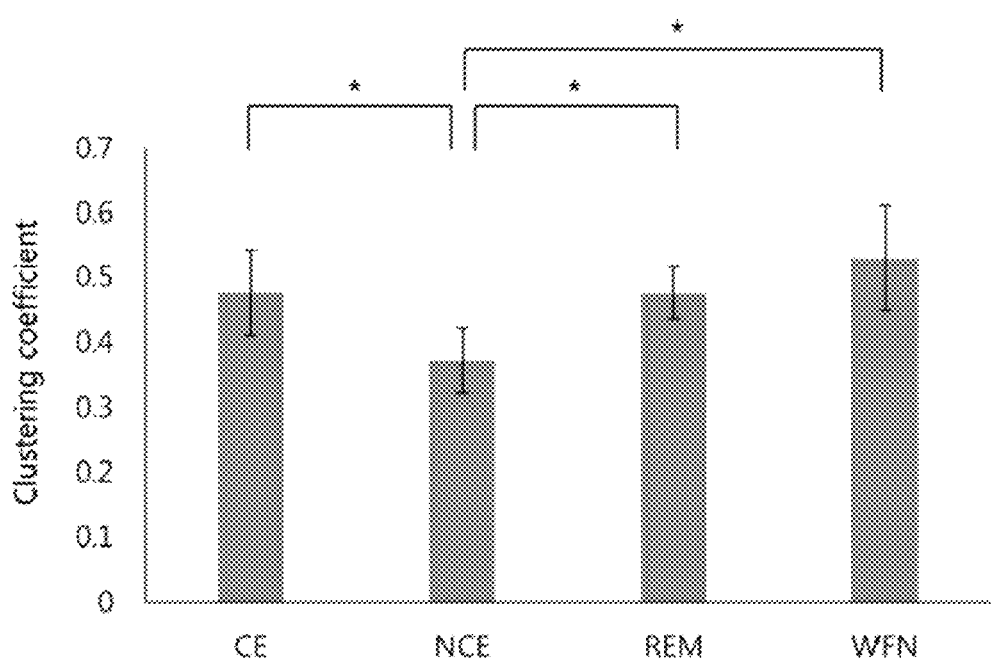
FIG. 4 is a graph showing a change in clustering coefficient depending on the stage of sleep classified into a CE state and a NCE state of a NREM sleep state in accordance with various embodiments described herein.

FIG. 4 is a graph showing a change in clustering coefficient depending on the stage of sleep classified into a CE state and a NCE state of a NREM sleep state in accordance with various embodiments described herein.

Figure 5:
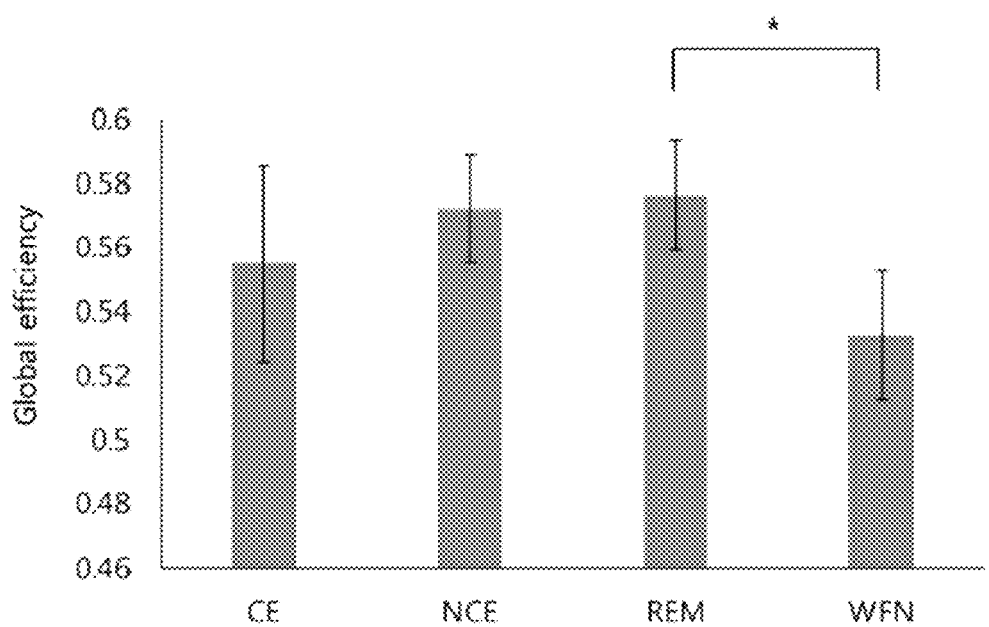
FIG. 5 is a graph showing a change in global efficiency depending on the stage of sleep classified into a WFN state or a REM sleep state.

FIG. 5 is a graph showing a change in global efficiency depending on the stage of sleep classified into a WFN state or a REM sleep state.

Referring to FIG. 3 through FIG. 5, I marked on each bar graph represents a standard deviation, and an asterisk (*) indicates a group in which two states represented by respective bars have a significant statistical difference (*<0.05), i.e., only two states indicated by * can be identified.

Referring to FIG. 3, if the strength value is equal to or higher than 17, the stage of sleep corresponds to the NREM sleep state including the CE state and the NCE state, and if the strength value is equal to or lower than 16.5, the stage of sleep corresponds to the REM sleep state and the WFN state.

For example, if the strength value increases, the stage of sleep may be identified as the NREM sleep state. In this case, if an index corresponding to a criterion to determine the degree of segregation of brain network increases, the stage of sleep may be identified as the CE state in the NREM sleep state.

For example, if the clustering coefficient value which is a criterion to determine the degree of segregation of brain network increases, the stage of sleep may be the CE state in the NREM sleep state, and if the clustering coefficient value decreases, the stage of sleep may be the NCE state in the NREM sleep state. Referring to FIG. 4, it can be seen that the clustering coefficient value is lower in the NCE state than in the CE state.

That is, as shown in FIG. 2B, in the firstly identified NREM sleep state, the CE state and the NCE state can be secondarily identified based on a value corresponding to the criterion to determine the degree of segregation of brain network (S136).

Further, if the strength value decreases, the stage of sleep may be identified as the WFN state and the REM sleep state. In this case, if an index corresponding to a criterion to determine the degree of integration of brain network increases, the stage of sleep may be identified as the REM sleep state.

For example, if the global efficiency value which is a criterion to determine the degree of integration of brain network increases, the stage of sleep may be the REM sleep state, and if the global efficiency value decreases, the stage of sleep may be the WFN state. Referring to FIG. 5, it can be seen that the global efficiency value is lower in the WFN state than in the REM sleep state.

That is, as shown in FIG. 2B, in the firstly identified WFN state and REM sleep state, the REM sleep state and the WFN state can be secondarily identified based on a value corresponding to the criterion to determine the degree of integration of brain network (S137).

Figure 6:
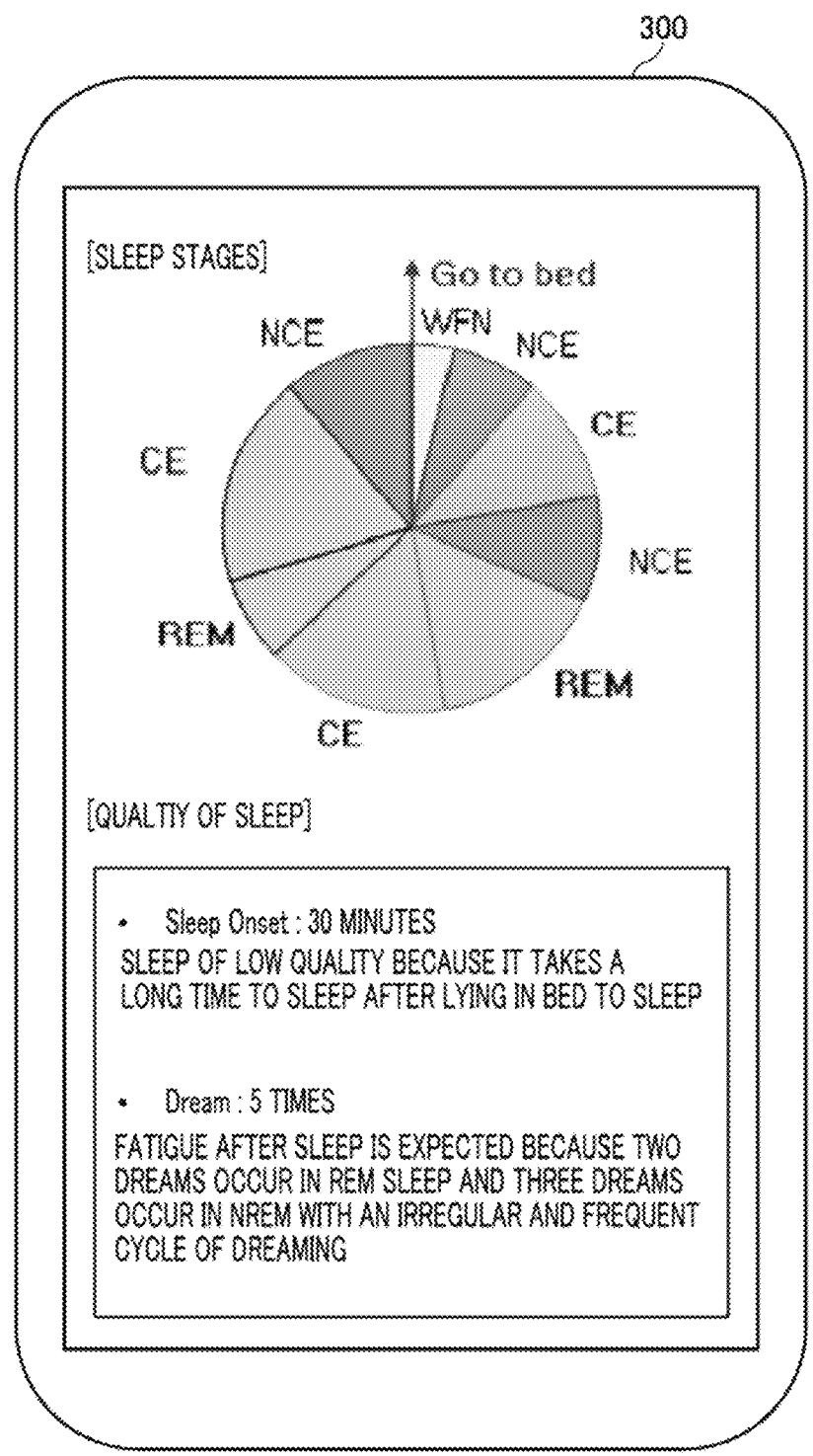
FIG. 6 is an example depiction of a user interface that displays a user's stage of sleep determined by a sleep inducing apparatus based on the level of consciousness using brain connectivity in accordance with various embodiments described herein.

FIG. 6 is an example depiction of a user interface that displays the user's stage of sleep determined by a sleep inducing apparatus based on the level of consciousness and using brain connectivity in accordance with various embodiments described herein.

Referring to FIG. 6, the user interface may provide a graph showing changes in sleep stage of the user in sequence of time as determined by the sleep inducing apparatus 200. Further, the user interface may receive a comment about the quality of sleep in which the number of dreams in the REM sleep state where most of dreams occur and the state of dreaming (CE state) in the NREM sleep state is also accurately analyzed.

Therefore, the stages of sleep can be determined more accurately based on the level of consciousness by understanding interactions between different regions through brain network analysis and thus understating the stage of dreaming in NREM sleep, which has not been measured. This technology for accurately determining the stages of sleep will provide important factors in measuring the quality of sleep of the user and understanding sleep disorders.

Figure 7:
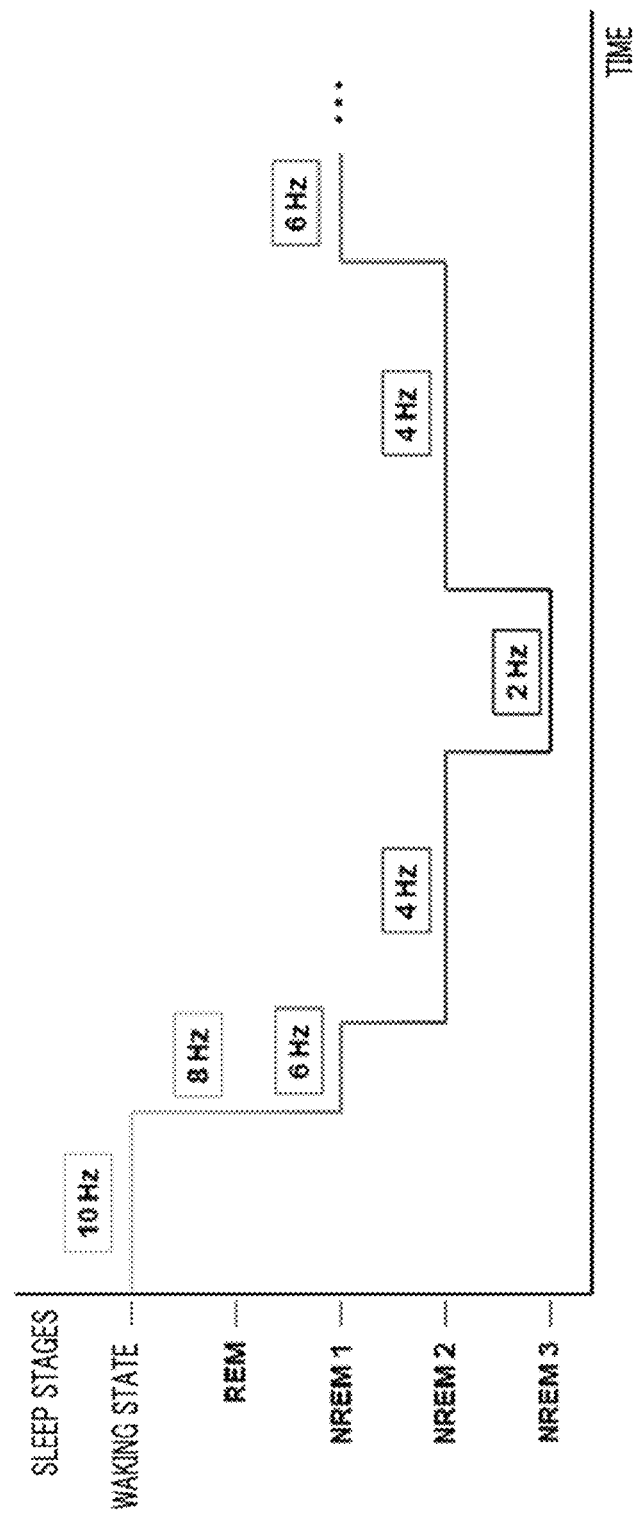
FIG. 7 is a graph showing a target frequency of a binaural beat for respective stages of sleep in accordance with various embodiments described herein.
Figure 8:
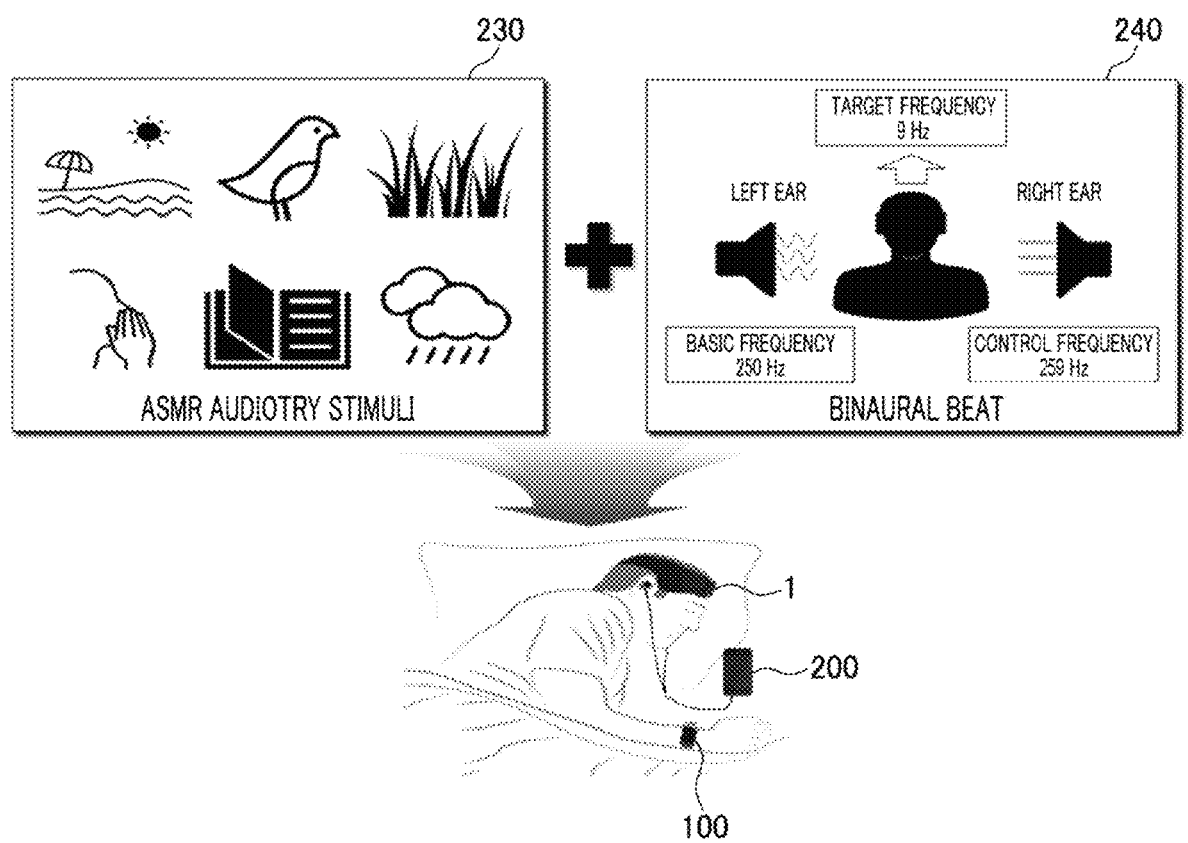
FIG. 8 is an example depiction showing a process for providing the user with auditory stimulus information as a combination of ASMR information and a binaural beat in accordance with various embodiments described herein.
Figure 9:
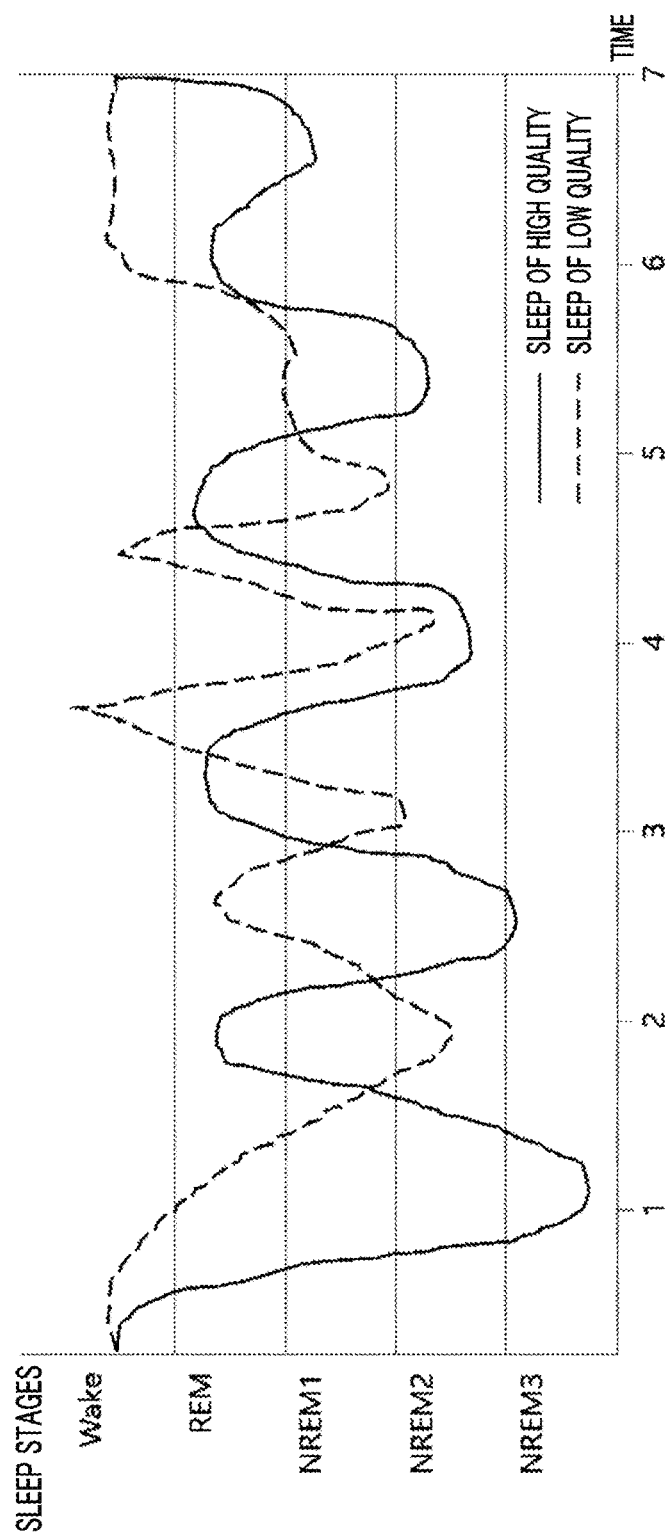
FIG. 9 is a graph provided to explain a sleep pattern depending on the quality of sleep in accordance with various embodiments described herein.

FIG. 7 is a graph showing a target frequency of a binaural beat for respective stages of sleep in accordance with various embodiments described herein. FIG. 8 is an example depiction showing a process for providing the user with auditory stimulus information as a combination of ASMR information and a binaural beat in accordance with various embodiments described herein. FIG. 9 is a graph provided to explain a sleep pattern depending on the quality of sleep in accordance with various embodiments described herein.

Referring to FIG. 7, the stages of sleep can be classified into a waking state (WFN state), a REM (Rapid Eye Movement) sleep state, a NREM1 (NREM: Non Rapid Eye Movement) sleep state, a NREM2 sleep state, and a NREM3 sleep state.

The sleep stage determination unit 220 may automatically classify the current stage of sleep in real time based on the start time of sleep, the start time and end time of each stage of sleep, and a frequency of the stage of sleep on the basis of information analyzed by the brain network analysis unit 215. For example, the stages of sleep may be classified using machine learning algorithms such as a support vector machine, a random forest classifier, an autoencoder, a hidden markov model, a linear discriminant analysis, and the like.

A personalized auditory stimulus may be presented according to the result of sleep stage analysis. When an auditory stimulus is presented, the audible frequency range for humans needs to be considered. The audible frequency range for humans is typically given as being between 20 Hz and 20,000 Hz. In the present disclosure, an auditory stimulus having a frequency of less than 20 Hz which is lower than the audible frequency range is given to a sleeping person. Thus, a binaural beat is used.

The binaural beat generation unit 240 may generate a target frequency, which is gradually decreased by a predetermined value, for REM sleep state, NREM1 sleep state, NREM2 sleep state, and NREM3 sleep state in sequence based on a frequency in a waking state. Herein, the target frequency refers to a frequency difference between two different sine waves when the two sine waves are provided to the two ears of the user 1. That is, a frequency of a brain signal of the user may be induced to the target frequency with the binaural beat. For example, if a sound of 250 Hz is presented to the left ear and a sound of 259 Hz is presented to the right ear, a brain signal is synchronized with a sound of 9 Hz corresponding to a frequency difference between the two sounds in the brain. In this process, 9 Hz of the brain signal is amplified. However, such an effect is not exhibited since the sounds are heard as overlapping when provided through a single speaker. Therefore, sounds having different frequencies may be provided to the two ears of the user 1 through a stimulus presentation unit 260 including earphones or a headset to exhibit the effect of a binaural beat.

For example, if a waking user starts the sleep inducing system 10 to sleep, the NREM1 stage, which is the first stage of sleep, needs to be induced. In this case, a binaural beat has a frequency corresponding to alpha waves (8 Hz to 13 Hz) and theta waves (4 Hz to 8 Hz). Desirably, the binaural beat may be provided with a frequency gradually decreased by 2 Hz. This is because a sharp decrease in frequency may cause side effects such as headache or the like. When the brain signal of the user 1 has a frequency matched to the target frequency, the binaural beat with a frequency decreased by 2 Hz may be provided.

For example, as shown in FIG. 7, when the user is in a waking state, a stimulus of 8 Hz corresponding to theta waves is provided to induce the NREM1 stage. When a frequency of the brain signal is matched to 8 Hz, the frequency of the stimulus is decreased by 2 Hz. Thus, a stimulus of 6 Hz is provided. If the NREM1 stage is maintained for an appropriate period of time, a stimulus of 4 Hz corresponding to a lower frequency of theta waves is provided to induce the NREM2 stage and a stimulus of 2 Hz corresponding to delta waves (~4 Hz) is provided to induce the NREM3 stage. In the case of 7 to 8 hours of sleep, 4 to 5 cycles each including deep and light sleep stages are repeated. Therefore, in the NREM3 stage, the stimulus of 4 Hz may be provided again to induce the NREM2 stage and the stimuli of 6 Hz and 8 Hz may be provided to induce the NREM1 stage.

That is, the sleep inducing apparatus 200 provides a target frequency, which is a frequency difference between auditory stimuli presented to the two ears of the user 1, based on a frequency of a bio-signal of the user in a waking state with closed eyes as analyzed by the sleep stage determination unit 220 and thus adjusts brain waves of the user 1 to induce sleep.

Referring to FIG. 8, the ASMR auditory stimulus generation unit 230 may generate an auditory stimulus that causes an ASMR that is a sensory experience or response, such as metal stability or pleasure, to a sensory stimulus. Thus, when hearing beep sounds such as a binaural beat, the user 1 may feel reduced discomfort and thus can be induced to a stable state in which the user 1 can sleep.

For example, ASMR information may include the sound of waves, the sound of rain, the sound of turning pages, wind noise, sounds of bugs, and sounds of tapping on an object.

The stimulus combination unit 250 may randomly select one of the sounds included in the ASMR information and may combine the selected sound with a binaural beat. Auditory stimulus information may be a combination of ASMR information having a single frequency and a binaural beat having two frequencies with a difference corresponding to a target frequency.

Further, the stimulus combination unit 250 determines whether the ASMR information randomly selected while analyzing a bio-signal of the user 1 in real time induces the user 1 to have mental stability. If the stimulus combination unit 250 determines that the selected ASMR information does not induce the user 1 to have mental stability, the stimulus combination unit 250 determines may provide another non-selected sound included in the ASMR information.

FIG. 8 illustrates an example of the system 10 that provides the auditory stimulus information as a combination of ASMR information and a binaural beat to the user 1 to induce sleep. For example, the user 1 may hear a combination of two stimuli through the stimulus presentation unit 260, and ASMR information may be presented equally to the two ears but a binaural beat with different frequencies divided into a basic frequency and a control frequency (target frequency) may be provided.

Herein, the stimulus presentation unit 260 provides the two ears of the user with the auditory stimulus information provided from the sleep inducing apparatus 200 and may be an external audio apparatus including earphones or a headset.

That is, the stimulus presentation unit 260 combines an auditory stimulus generated by the ASMR auditory stimulus generation unit 230 and an auditory stimulus generated by the binaural beat generation unit 240 and provides the two kinds of auditory stimuli to the user. Thus, the stimulus presentation unit 260 can induce mental stability and also activate brain signals corresponding to the stages of sleep which are different for each person.

The feedback unit 270 determines whether or not the induced stage of sleep is maintained at an appropriate proportion with respect to total sleep time to determine whether or not to induce the next stage of sleep and then gives feedback thereon.

FIG. 9 shows sleep patterns for sleep of high quality and sleep of low quality, respectively. Herein, appropriate proportions of sleep stages NREM1: NREM2: NREM3: REM may be about 5%: 45%: 25%: 25%. For example, as for a person who suffers from insomnia or has trouble sleeping, the proportion of the NREM2 stage is abnormally high. Therefore, in order to improve the quality of sleep, an auditory stimulus may be presented so that the stages of sleep can be maintained at the above-described proportions, respectively.

For example, the sleep inducing apparatus 200 may evaluate the quality of sleep using various indices. The evaluation indices may include the length of time that it takes to transition to NREM1 (sleep onset latency), the number of wakes after sleep onset, total sleep time, duration of deep sleep (NREM3), sleep efficiency, and the like. Further, subjective sleep satisfaction can also be an important index in evaluating the quality of sleep. The quality of sleep of the user can be evaluated based on these indices.

The following method is performed by the above-described system 10. Therefore, the above descriptions may be applied to the following method, even though they are omitted hereinafter.

Hereinafter, a method for inducing sleep according to an embodiment of the present disclosure includes a process for measuring the stages of sleep based on the level of consciousness using brain connectivity which will be described with reference to FIG. 10, and a process for inducing sleep based on an auditory stimulus according to real-time sleep stage classification which will be described with reference to FIG. 11.

Figure 10:
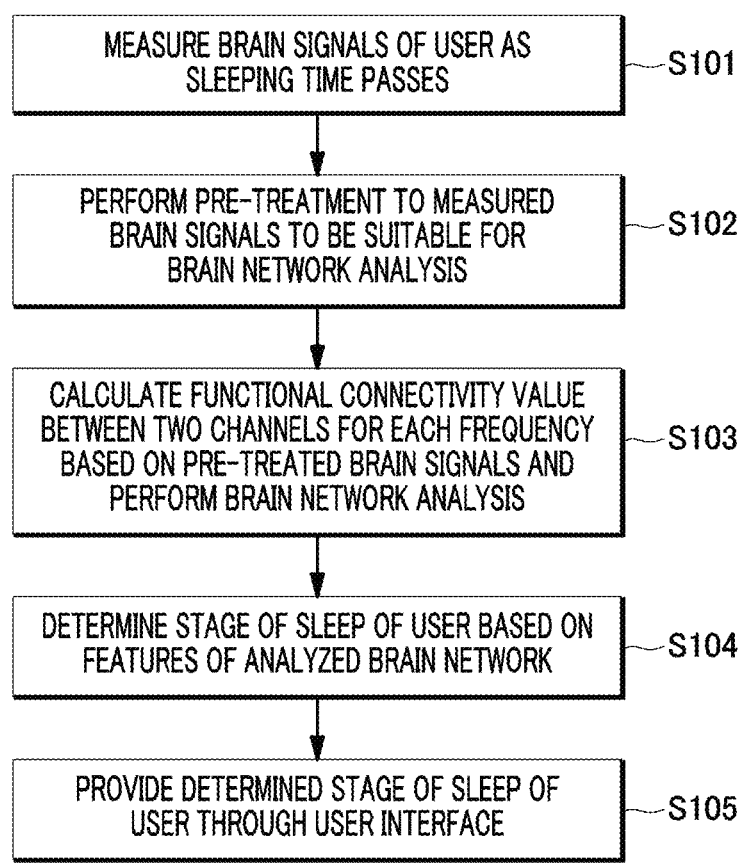
FIG. 10 is a flowchart provided to explain a method for determining the stages of sleep based on the level of consciousness using brain connectivity in accordance with various embodiments described herein.

FIG. 10 is a flowchart provided to explain a method for measuring the stages of sleep based on the level of consciousness using brain connectivity in accordance with various embodiments described herein.

Referring to FIG. 10, the method for measuring the stages of sleep by the system 10 includes acquiring brain signals of a user as sleeping time passes (S101), performing pre-treatment to the acquired brain signals to be suitable for brain network analysis (S102), calculating a functional connectivity value between two channels for each frequency based on the pre-treated brain signals and performing brain network analysis (S103), determining the stage of sleep of the user based on features of the analyzed brain network (S104), and providing the determined stage of sleep of the user through a user interface (S105).

The process of performing the pre-treatment includes removing noise from the acquired brain signals and performing filtering to the noise-removed brain signals in a specific frequency band related to sleep or consciousness.

The process of performing the brain network analysis includes calculating a functional connectivity value between two channels based on amplitude and phase values of the respective brain signals, applying a threshold value to determine whether or not the calculated functional connectivity value has significant connectivity, and calculating a brain network value based on the graph theory.

Herein, the functional connectivity value is a criterion to determine the degree of synchronization of phases between brain signals of the two channels and may include one or more of a phase locking value, a phase lag index, a weighted phase lag index, an imaginary coherence, and a synchronization likelihood. The threshold value may be set to a value with the greatest difference between a global efficiency and a local efficiency calculated from multiple random matrixes.

Further, the brain network values may be a criterion to determine the degree of integration of brain network and may be quantified into one or more of global efficiency and characteristic path length. The brain network values may be a criterion to determine the degree of segregation of brain network and may be quantified into one or more of local efficiency, clustering coefficient, transitivity, and modularity. The brain network values may be a criterion to determine the degree of functional connectivity between one of multiple nodes in a brain network and the other nodes and may be quantified into one or more of node degree and strength.

The process of determining the stage of sleep of the user includes determining the stages of sleep of the user as sleeping time passes. Herein, the stages of sleep may be identified as WFN state, REM sleep state, and CE state and NCE state in NREM sleep state based on the brain network value. If the strength value increases, the stage of sleep may be identified as the NREM sleep state. In this case, if an index corresponding to a criterion to determine the degree of segregation of brain network increases, the stage of sleep may be identified as the CE state in the NREM sleep state. If the strength value decreases, the stage of sleep may be identified as the WFN state or the REM sleep state. In this case, if an index corresponding to a criterion to determine the degree of integration of brain network increases, the stage of sleep may be identified as the REM sleep state.

Figure 11:
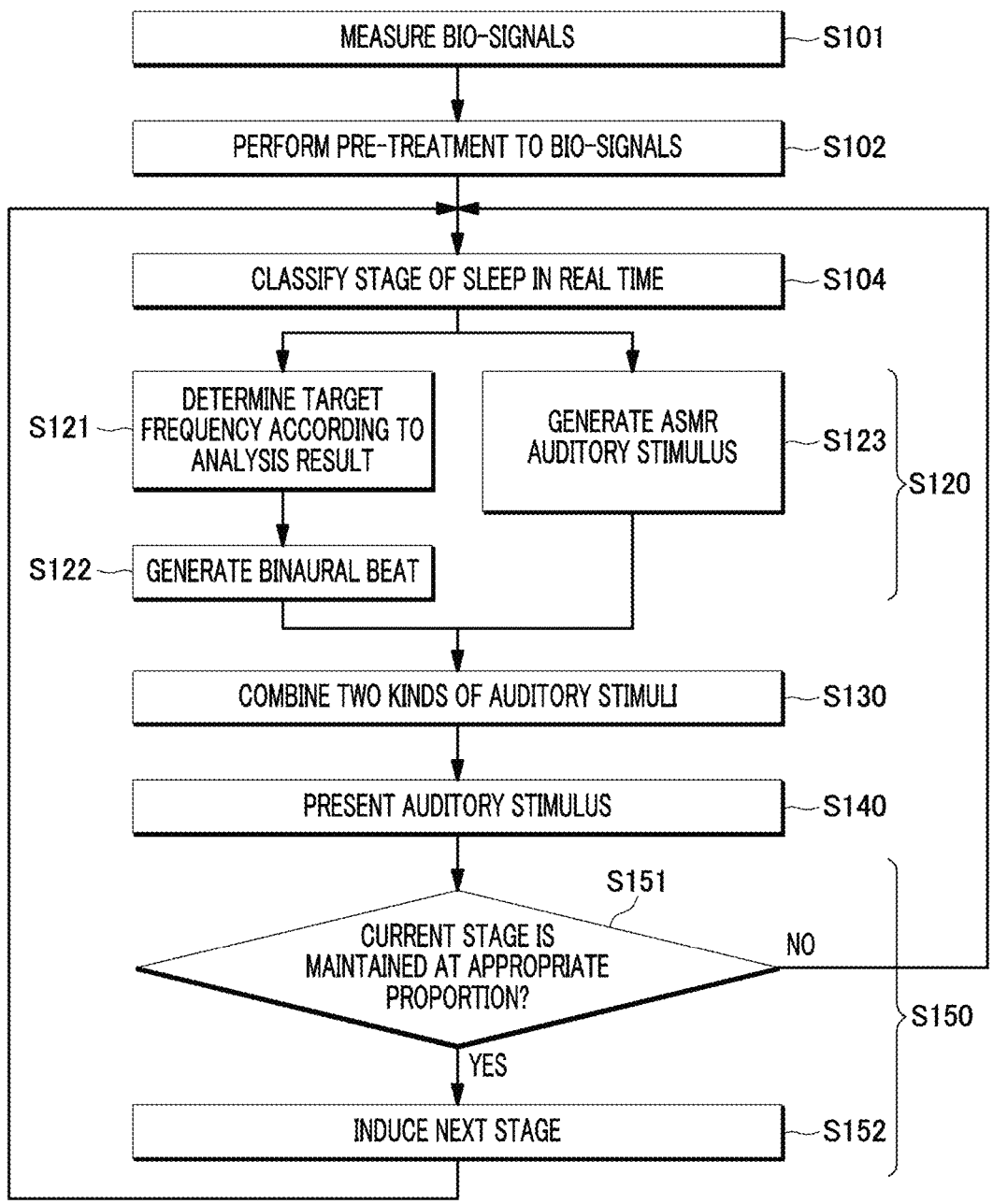
FIG. 11 is a flowchart provided to explain a method for inducing sleep by the sleep inducing system in accordance with various embodiments described herein.

FIG. 11 is a flowchart provided to explain a method for inducing sleep by the sleep inducing system in accordance with various embodiments described herein.

Referring to FIG. 11, the method for inducing sleep based on an auditory stimulus by the system 10 includes determining the stage of sleep of the user based on features of the analyzed brain network (S104), determining a target frequency according to the determined stage of sleep and generating a binaural beat with which the brain signals of the user are induced to the target frequency (S120), combining the generated binaural beat with autonomous sensory meridian response (ASMR) information (S130), providing the combined auditory stimulus information to the user (S140), and determining whether the current stage of sleep of the user is maintained at an appropriate proportion with respect to total sleep time, determining whether or not to induce the next stage of sleep, and performing feedback according to the result of determination (S150).

As described above, before the process of determining the stage of sleep (S104), bio-signals may be measured using at least one of a smart band, a smartphone, a multi-channel cap for brain signal measurement, and a headband-type brain signal measurement device (S101). Further, the pre-treatment including removing noise from the bio-signals and performing filtering to the noise-removed bio-signals in a specific frequency band related to sleep or consciousness may be performed (S102). Herein, the bio-signals may include one or more of brain signal, pulse, heart rate, and movement of the body. The stages of sleep can be classified into a waking state, a REM (Rapid Eye Movement) sleep state, a NREM1 (NREM: Non Rapid Eye Movement) sleep state, a NREM2 sleep state, and a NREM3 sleep state.

In process S120, a target frequency may be determined according to the determined stage of sleep (S121), a binaural beat with which the brain signals of the user are induced to the target frequency may be generated (S122), and ASMR information may be generated (S124). Herein, the ASMR information may include the sound of waves, the sound of rain, the sound of turning pages, wind noise, sounds of bugs, and sounds of tapping on an object.

In the process of generating the binaural beat (S120), the target frequency may be gradually decreased by a predetermined value for REM sleep state, NREM1 sleep state, NREM2 sleep state, and NREM3 sleep state in sequence based on a frequency in a waking state.

In the process of combining the ASMR information (S130), one of the sounds included in the ASMR information may be selected randomly and combined with a binaural beat.

In the process of providing the auditory stimulus information to the user (S140), the auditory stimulus information may be provided to the two ears of the user through an audio apparatus including earphones or a headset. Herein, the auditory stimulus information may be a combination of ASMR information having a single frequency and a binaural beat having two frequencies with a difference corresponding to a target frequency.

It is possible to determine whether the ASMR information randomly selected in the process of analyzing a bio-signal of the user in real time (S101) induces the user to have mental stability. If it is determined that the selected ASMR information does not induce the user to have mental stability, another sound included in the ASMR information but not selected in process S130 may be provided.

In the process of performing the feedback (S150), it is possible to determine whether the current stage of sleep of the user is maintained at an appropriate proportion with respect to total sleep time (S151). For example, if the current stage of sleep of the user is maintained at an appropriate proportion, the processes from S104 may be repeated in sequence to induce the next stage of sleep (S152). If the current stage of sleep of the user is not maintained at an appropriate proportion, the processes from S104 may be repeated in sequence to maintain the current stage of sleep.

The embodiments of the present disclosure can be embodied in a storage medium including instruction codes executable by a computer such as a program module executed by the computer. The storage medium includes a computer-readable medium, and the computer-readable medium can be any usable medium which can be accessed by the computer and includes all volatile/non-volatile and removable/non-removable media. Further, the computer-readable medium may include all computer storage media. The computer storage media include all volatile/non-volatile and removable/non-removable media embodied by a certain method or technology for storing information such as computer-readable instruction code, a data structure, a program module or other data. The method and system of the present disclosure have been explained in relation to a specific embodiment, but their components or a part or all of their operations can be embodied by using a computer system having general-purpose hardware architecture.

The above description of the present disclosure is provided for the purpose of illustration, and it would be understood by a person with ordinary skill in the art that various changes and modifications may be made without changing technical conception and essential features of the present disclosure. Thus, it is clear that the above-described embodiments are illustrative in all aspects and do not limit the present disclosure. For example, each component described to be of a single type can be implemented in a distributed manner. Likewise, components described to be distributed can be implemented in a combined manner.

The scope of the present disclosure is defined by the following claims rather than by the detailed description of the embodiment. It shall be understood that all modifications and embodiments conceived from the meaning and scope of the claims and their equivalents are included in the scope of the present disclosure.

EXPLANATION OF REFERENCE NUMERALS

100: Bio-signal measurement unit
200: Sleep inducing apparatus
210: Pre-treatment unit
215: Brain network analysis unit
220: Sleep stage determination unit
230: ASMR auditory stimulus generation unit
240: Binaural beat generation unit
250: Stimulus combination unit
260: Stimulus presentation unit
270: Feedback unit
300: Feedback presentation unit

We claim:

1. A method for inducing sleep by a sleep inducing system, comprising:
acquiring brain signals of a user as sleeping time passes;
calculating a functional connectivity value between two channels for each frequency based on the acquired brain signals and performing brain network analysis;
determining a stage of sleep of the user based on the functional connectivity value and the brain network analysis;
determining a target frequency according to the determined stage of sleep and generating a binaural beat with which the brain signals of the user are induced to the target frequency;
combining the generated binaural beat with autonomous sensory meridian response (ASMR) information;
providing an auditory stimulus information combined with the binaural beat and the ASMR information to the user; and
determining whether the determined stage of sleep of the user is maintained at an appropriate proportion with respect to total sleep time, determining whether or not to induce the stage of sleep of next order, and performing feedback according to a result of determination,
wherein the ASMR information includes sounds of waves, sounds of rain, sounds of turning pages, wind noise, sounds of bugs, and sounds of tapping on an object.

2. The method for inducing sleep of claim 1, further comprising:
providing the determined stage of sleep of the user through a user interface.

3. The method for inducing sleep of claim 1, further comprising:
performing pre-treatment to the brain signals to be suitable for the brain network analysis after said acquiring the brain signals of the user,
wherein said performing the pre-treatment includes:
removing noise from the acquired brain signals; and
performing filtering to the noise-removed brain signals in a specific frequency band related to sleep or consciousness.

4. The method for inducing sleep of claim 1,
wherein said calculating the functional connectivity value includes:
calculating the functional connectivity value between the two channels based on amplitudes and phase values of the brain signals; and
applying a threshold value to determine whether or not the calculated functional connectivity value has significant connectivity and calculating a brain network value based on a graph theory, and
the functional connectivity value is a criterion to determine a degree of synchronization of phases between brain signals of the two channels and includes one or more of a phase locking value, a phase lag index, a weighted phase lag index, an imaginary coherence, and a synchronization likelihood, and
the threshold value is set to a value with a greatest difference between a global efficiency and a local efficiency calculated from multiple random matrixes.

5. The method for inducing sleep of claim 4,
wherein the brain network value is a criterion to determine a degree of integration of the brain network and is quantified into one or more of the global efficiency and a characteristic path length,
the brain network value is a criterion to determine a degree of segregation of the brain network and is quantified into one or more of the local efficiency, a clustering coefficient, transitivity, and modularity, and
the brain network value is a criterion to determine a degree of functional connectivity between one of multiple nodes in the brain network and other nodes and is quantified into one or more of node degree and a strength value.

6. The method for inducing sleep of claim 5,
wherein said determining the stage of sleep of the user includes:
determining stages of sleep of the user as sleeping time passes, and the stages of sleep are identified as Wakefulness (WFN) state, Rapid Eye Movement (REM) sleep state, and Conscious Experience (CE) state and No Conscious Experience (NCE) state in Non Rapid Eye Movement (NREM) sleep state based on the brain network value, and when the strength value increases, the stage of sleep is identified as the NREM sleep state, and in this case of the strength value increasing, when an index corresponding to the criterion to determine the degree of segregation of the brain network increases, the stage of sleep is identified as the CE state in the NREM sleep state, and when the strength value decreases, the stage of sleep is identified as the WFN state or the REM sleep state, and in this case of the strength value decreasing, when an index corresponding to the criterion to determine the degree of integration of the brain network increases, the stage of sleep is identified as the REM sleep state.

7. The method for inducing sleep of claim 6,
wherein the NREM sleep state is classified into NREM1 sleep state, NREM2 sleep state, and NREM3 sleep state, and
in said determining the target frequency,
the target frequency is gradually decreased by a predetermined value for the REM sleep state, the NREM1 sleep state, the NREM2 sleep state, and the NREM3 sleep state in sequence based on a frequency in the WFN state.

8. The method for inducing sleep of claim 1, wherein
in said combining the generated binaural beat with the ASMR information,
one of the sounds included in the ASMR information is selected randomly and combined with the binaural beat.

9. The method for inducing sleep of claim 8,
wherein the auditory stimulus information is a combination of the ASMR information having a single frequency and the binaural beat having two frequencies with a difference corresponding to the target frequency, and
in said providing the auditory stimulus information combined with the binaural beat and the ASMR information to the user,
the auditory stimulus information is provided to the two ears of the user through an external audio apparatus including earphones or a headset.

10. The method for inducing sleep of claim 9, further comprising:
determining whether the ASMR information randomly selected in a process of analyzing the stage of sleep induces the user to have mental stability,
wherein when it is determined that the selected ASMR information does not induce the user to have mental stability, another non-selected sound included in the ASMR information is provided.

11. A sleep inducing system, comprising:
a memory in which a program configured to perform a method for inducing sleep is stored; and
a processor that executes the program,
wherein upon execution of the program,
the processor
acquires brain signals of a user as sleeping time passes,
calculates a functional connectivity value between two channels for each frequency based on the acquired brain signals and performs brain network analysis,
determines a stage of sleep of the user based on the functional connectivity value and the brain network analysis,
determines a target frequency according to the determined stage of sleep and generates a binaural beat with which the brain signals of the user are induced to the target frequency,
combines the generated binaural beat with autonomous sensory meridian response (ASMR) information,
provides an auditory stimulus information combined with the binaural beat and the ASMR information to the user, and
determines whether the determined stage of sleep of the user is maintained at an appropriate proportion with respect to total sleep time, determines whether or not to induce the stage of sleep of next order, and performs feedback according to a result of determination,
wherein the ASMR information includes sounds of waves, sounds of rain, sounds of turning pages, wind noise, sounds of bugs, and sounds of tapping on an object.

12. The sleep inducing system of claim 11,
wherein the processor provides the determined stage of sleep of the user through a user interface.

13. The sleep inducing system of claim 11,
wherein the processor performs pre-treatment to the brain signals to be suitable for the brain network analysis,
removes noise from the acquired brain signals, and
performs filtering to the noise-removed brain signals in a specific frequency band related to sleep or consciousness.

14. The sleep inducing system of claim 11,
wherein the processor calculates the functional connectivity value between the two channels based on amplitudes and phase values of the brain signals, and
applies a threshold value to determine whether or not the calculated functional connectivity value has significant connectivity and calculates a brain network value based on a graph theory, and
the functional connectivity value is a criterion to determine a degree of synchronization of phases between brain signals of the two channels and includes one or more of a phase locking value, a phase lag index, a weighted phase lag index, an imaginary coherence, and a synchronization likelihood, and
the threshold value is set to a value with a greatest difference between a global efficiency and a local efficiency calculated from multiple random matrixes.

15. The sleep inducing system of claim 14,
wherein the brain network value is a criterion to determine a degree of integration of the brain network and is quantified into one or more of the global efficiency and a characteristic path length,
the brain network value is a criterion to determine a degree of segregation of the brain network and is quantified into one or more of the local efficiency, a clustering coefficient, transitivity, and modularity, and
the brain network value is a criterion to determine a degree of functional connectivity between one of multiple nodes in the brain network and other nodes and is quantified into one or more of node degree and a strength value.

16. The sleep inducing system of claim 15,
wherein the processor determines the stage[s] of sleep of the user as sleeping time passes, and
stages of sleep are identified as Wakefulness (WFN) state, Rapid Eye Movement (REM) sleep state, and Conscious Experience (CE) state and No Conscious Experience (NCE) state in Non Rapid Eye Movement (NREM) sleep state based on the brain network value, and when the strength value increases, the stage of sleep is identified as the NREM sleep state, and in this case of the strength value increasing, when an index corresponding to the criterion to determine the degree of segregation of the brain network increases, the stage of sleep is identified as the CE state in the NREM sleep state, and when the strength value decreases, the stage of sleep is identified as the WFN state or the REM sleep state, and in this case of the strength value decreasing, when an index corresponding to the criterion to determine the degree of integration of the brain network increases, the stage of sleep is identified as the REM sleep state.

17. The sleep inducing system of claim 16, wherein the NREM sleep state is classified into NREM1 sleep state, NREM2 sleep state, and NREM3 sleep state, and the processor gradually decreases the target frequency by a predetermined value for the REM sleep state, the NREM1 sleep state, the NREM2 sleep state, and the NREM3 sleep state in sequence based on a frequency in the WFN state.

18. The sleep inducing system of claim 11, wherein the processor randomly selects one of the sounds included in the ASMR information and combines the selected sound with the binaural beat.

19. The sleep inducing system of claim 18, wherein the auditory stimulus information is a combination of the ASMR information having a single frequency and the binaural beat having two frequencies with a difference corresponding to the target frequency, and the processor provides the auditory stimulus information to the two ears of the user through an external audio apparatus including earphones or a headset.

20. The sleep inducing system of claim 19, wherein the processor determines whether the ASMR information randomly selected in a process of analyzing the stage of sleep induces the user to have mental stability, and when the processor determines that the selected ASMR information does not induce the user to have mental stability, another non-selected sound included in the ASMR information is provided.

* * * * *